(12) United States Patent
Enge

(10) Patent No.: US 8,416,492 B2
(45) Date of Patent: Apr. 9, 2013

(54) BALANCING APPARATUS FOR A SURGICAL MICROSCOPE

(75) Inventor: Stefan Enge, Balgach (CH)

(73) Assignee: Leica Instruments (Singapore) Pte. Ltd., Singapore (SG), `

( * ) Notice: Subject to any disclaimer, the term of this patent is extended or adjusted under 35 U.S.C. 154(b) by 512 days.

(21) Appl. No.: 12/371,518

(22) Filed: Feb. 13, 2009

(65) Prior Publication Data

US 2009/0219613 A1    Sep. 3, 2009

(30) Foreign Application Priority Data

Feb. 28, 2008 (DE) .......................... 10 2008 011 638

(51) Int. Cl.
*G02B 21/00* (2006.01)

(52) U.S. Cl.
USPC ............................. 359/384; 359/368; 359/382

(58) Field of Classification Search ........... 359/368–394
See application file for complete search history.

(56) References Cited

U.S. PATENT DOCUMENTS

| | | | |
|---|---|---|---|
| 4,362,355 A | | 12/1982 | Takahashi |
| 4,577,141 A | * | 3/1986 | Saiki et al. ..................... 318/590 |
| 4,766,465 A | * | 8/1988 | Takahashi ........................ 355/53 |
| 5,213,293 A | * | 5/1993 | Muentener et al. ....... 248/123.11 |
| 5,991,005 A | * | 11/1999 | Horikawa et al. ................ 355/53 |
| 6,592,086 B1 | * | 7/2003 | Sander .................... 248/123.11 |
| 6,630,668 B1 | * | 10/2003 | Cramer et al. .................... 850/2 |
| 8,132,769 B2 | * | 3/2012 | Metelski .................. 248/281.11 |
| 2002/0108874 A1 | | 8/2002 | Metelski | 
| 2009/0218455 A1 | * | 9/2009 | Metelski .................... 248/122.1 |

FOREIGN PATENT DOCUMENTS

| | | |
|---|---|---|
| DE | 1 901 180 | 11/1969 |
| DE | 101 33 018 | 1/2003 |
| EP | 0476551 | 3/1992 |
| EP | 1 193 438 | 4/2002 |

OTHER PUBLICATIONS

Related non-published U.S. Appl. No. 12/371,492, filed Feb. 13, 2009 and assigned to Leica Microsystems (Schweiz) AG.
Related non-published U.S. Appl. No. 12/371,440, filed Feb. 13, 2009 and assigned to Leica Microsystems (Schweiz) AG.
Related non-published U.S. Appl. No. 12/391,116, filed Feb. 20, 2009 and assigned to Leica Microsystems (Schweiz) AG.

* cited by examiner

*Primary Examiner* — Thong Nguyen
(74) *Attorney, Agent, or Firm* — Schlee IP International, P.C.; Alexander R. Schlee

(57) ABSTRACT

A balancing apparatus for a surgical microscope is suggested for balancing an optics carrier that is held via a pivot support at a stand. The apparatus comprises a Y displacement unit comprising a first slide for displacement of the optics carrier in a Y direction and a Z displacement unit comprising a second slide for displacement of the optics carrier in a Z direction. Both slides are driven by motors. A selector switch enables an operator to select powering either the first motor or the second motor; and a forward-reverse switch enables the operator to select either the forward or the reverse driving mode for the motor powered by the selector switch and consequently establish the forward or the reverse driving mode for the first or second slide, respectively.

12 Claims, 5 Drawing Sheets

BALANCING APPARATUS FOR A SURGICAL MICROSCOPE

CROSS-REFERENCE TO RELATED APPLICATION

This application claims the priority of the German patent application DE 102008011638.6 having a filing date of Feb. 28, 2008, the entire content of which is herewith incorporated by reference.

BACKGROUND OF THE INVENTION

The invention relates to a balancing apparatus for a surgical microscope, mounted on a rotation axis (A axis) that is held via a pivot support on a stand. The surgical microscope is balanceable in the Y and the Z direction via a cross-slide (alternative common designation: A-B slide) in two spatial directions (horizontal and vertical spatial direction). A typical construction in accordance with these features is the Applicant's MC1 surgical microscope. A "stand" is to be understood for purposes of the invention as any apparatus that spaces a surgical microscope away from the floor.

As is known to one skilled in the art, surgical microscopes should be very easy to move, and quickly displaceable without a great expenditure of energy. To ensure that a surgical microscope does not move on its own once a position is established, the forces and moments occurring in any position must be equalized (balanced). If the surgical microscope is not sufficiently equalized, however, brakes or bracing devices must be present in order to hold the surgical microscope in its position. Such brakes or bracing devices disadvantageously increase the overall weight of the structure. The forces and moments should be balanced out even when brakes or bracing devices are present, however, in order to enable easy movement of the surgical microscope in three dimensions when the brakes are released or the bracing devices are removed.

On the other hand, the use of a surgical microscope normally involves utilization of a wide variety of different accessories (e.g. tubes, extensions, filters, auxiliary lenses, etc.). This results in most cases, however, in a shift of the overall center of gravity. As a result, the surgical microscope is no longer in equilibrium and must be balanced out again. The basic goal in this context is to keep the overall center of gravity on the pivot axis of the surgical microscope.

DE 10133018 A1 (of the same Applicant) describes one such arrangement; here again, an optics carrier along with a surgical microscope are rotatable about a horizontal rotation axis (A axis). They need to be balanced out with reference to this A axis so that when the brakes are released, a surgeon can as easily as possible, i.e. with as little resistance and torque as possible, rotate the optics carrier (and thus the surgical microscope) about this A axis. This rotation axis is usually configured on the lower part of the pivot support and is equipped with a brake unit or locking unit that prevents any rotary movement of the optics carrier, and therefore of the surgical microscope, with reference to the pivot support.

Installed between the optics carrier and the pivot support is a balancing unit with which the optics carrier along with the surgical microscope can be balanced out about the horizontal A axis in the Y and the Z direction. This balancing unit encompasses two slides that are arranged one above another. One of them is displaceable in the Y direction and the other in the Z direction, each by means of a displacement unit, and they can be immobilized in a position that is established. Arranged at the upper end of the pivot support is a further displacement unit that enables a displacement in the X direction (FIG. 2 of DE 10133018 A1).

The solutions in accordance with DE 10133018 A1 (FIGS. 2 and 3) have not yet appeared in practical use. A similar, older approach, however, has been disclosed by the Applicant's MC1 stand. With this approach, the Y-Z displacement unit made up of the two slides arranged one above another was mounted on the rotation axis in such a way that the Z slide was mounted directly on the rotation axis, and the Y slide was mounted on the one hand directly on the Z slide and on the other hand on the optics carrier. As in the case of the construction according to FIG. 2 of DE 10133018 A1, the X slide was mounted above the pivot support. This construction has proven substantially successful. It had one disadvantage, however: In order to enable sufficient balancing for the surgeon even in those system configurations in which, for example, assistant's tubes or lateral add-on units are to be attached to the optics carrier, the surgeon must carry out another balancing procedure each time such add-on units are installed or removed. For this, once the brake or locking system of the optics carrier relative to the A axis has been released, the surgeon must a) bring the optics carrier into a vertical position corresponding to a normal observation position of the surgical microscope; then
  b) rotate the balancing screw for displacement in the Y direction until, and in directions such that, the surgical microscope is balanced across the A axis in that position; then
  c) bring the optics carrier into a position that is horizontal with respect to the normal vertical observation position; then
  d) rotate the balancing screw for displacement in the Z direction until, and in such directions that, the surgical microscope is once again balanced across the A axis.

After completion of these balancing procedures, the microscope is completely balanced out with reference to the A axis, i.e. it can be pivoted across the A axis as if weightless.

The result of steps a) to d) with the above arrangement is, however, that the surgeon has his or her "hands full," and accordingly loses a great deal of time while changing the add-on units and afterward during the balancing procedure. An additional complication is that during a surgical operation, the balancing screws are located in the area that is "draped" (covered with a drape) during a surgical operation, so that the surgeon has difficulty reaching these screws or finds it almost impossible to actuate them through the drape.

An obvious approach to eliminating this problem would be to retrofit the MC1 with an automatic balancing apparatus that independently performs at least steps b) and d). An automatic balancing system of this kind would, however, make the configuration considerably more expensive. There is moreover no reason, for this practical application, to explore whether (or how) this might be technically achievable. As an alternative, ideal balancing could be dispensed with by attaining, as with other products on the market, correct positioning in the unbalanced state with an assistance apparatus using spring force or the like. Smooth motion of the surgical microscope would, however, thereby be limited. On the other hand, homogeneity of the movements would also thereby be reduced.

The problem described above is therefore the basis of the invention as a first object. The intention is thus to achieve a reduction in or simplification of the balancing procedures without expensive and complex automation of the balancing function about the A axis.

The MC1 of the existing art also exhibited a further problem, however:

In order, however, to enable sufficient balancing for the surgeon even, and especially, in those configurations of the system in which, for example, assistant's tubes or lateral add-on units are attached, a consequence of the known arrangement according to the MC1 is that these add-on units can collide, during the balancing procedure, with the slide that sits on the A axis and is responsible for vertical displacement. The freedom of movement of the surgical microscope was therefore previously limited in the case of the known unit. On the other hand, homogeneity of the movements was thereby also reduced, since complete balancing was not always possible.

In the past, in accordance with the existing art in the context of the MC1, in order to reduce this difficulty the procedure of balancing out in the Y and Z directions was made easier by attaching an add-on weight. The add-on weight, with its mass of approximately 3.5 kg, was attached on the side of the optics carrier located opposite the surgical microscope. The add-on units were thus balanced out across the A axis at least in terms of the Y direction (with the surgical microscope in the normal position; see step a) above).

The disadvantage of this known weight compensation is that it considerably increases the total weight, which results in increased inertia when pivoting. Installation or removal of this add-on weight also required additional effort. This method is therefore time-consuming, and moreover results in increased forces and moments on the stand as a whole because of the greater total weight (see e.g. EP-0476551 A1). The add-on weight in fact produces not only an increase in torque (moment of resistance to rotation) during the displacement procedure, but also greater friction in every bearing of the entire stand, thus increasing the overall inertia of the stand and limiting its mobility. Homogeneity of the movements of the stand is also thereby reduced. In addition, the dimensions of the carrier arms of the stand (and of all other load-bearing components) of course also had to be correspondingly enlarged, which in turn considerably increased the total weight of these components and thus also the cost of the stand.

In the most up-to-date surgical practice, surgical microscopes not only need to meet standard requirements in terms of optical quality, bright illumination, compact design, and maximum flexibility, but also must incorporate additional operational aspects. Consideration must now be given, for example, to the fact that the number of surgical operations per day has risen. The time needed to set up a surgical microscope for the next operation is becoming increasingly important. As an essential component of the operating-room infrastructure, the surgical microscope has a significant influence on costly preparation time.

The second object underlying the invention is therefore that of even further improving an apparatus that has been improved in accordance with the first object, which apparatus enables relatively faster, simpler, and complete balancing of the surgical microscope without an add-on weight and which can significantly reduce or eliminate the aforementioned disadvantages of the existing art. The intention is therefore for all possible configurations of the surgical microscope to be as easy as possible for the surgeon to balance out.

SUMMARY OF THE INVENTION

According to an aspect of the invention, a balancing apparatus for a surgical microscope for balancing an optics carrier is provided that carries optics of the surgical microscope, said optics carrier being held via a pivot support at a stand such that the balancing compensates for the use with and without a microscope holder holding the surgical microscope and with and without add-on units, wherein the balancing apparatus is arranged at the free end of the pivot support and comprises: a Y displacement unit comprising a first slide for displacement of the optics carrier in a Y direction, the first slide being driven by a remotely controllable first motor; a Z displacement unit comprising a second slide for displacement of the optics carrier in a Z direction by a second motor; a selector switch enabling an operator to select powering either the first motor or the second motor; and a forward-reverse switch enabling an operator to select either the forward or the reverse driving mode for the motor powered by the selector switch and consequently enabling the operator to select either the forward or the reverse driving mode of the first or second slide, respectively; wherein the first and second slides are integrated into a cross-slide that is rotatable around a rotation axis relative to the pivot support, wherein the first slide is arranged as part of the Y displacement unit transversely to the rotation axis alongside the pivot support and the second slide is arranged between the first slide and the optics carrier as part of the Z displacement unit, so that the weight of the second slide acts as a compensation weight across the rotation axis for locating common center of gravity G of the optics carrier with respective accessories and the Y and Z displacement units in the rotation axis; and the first slide of the cross-slide has a first guidance element and a first insert axially displaceable in that first guidance element, the first insert is secured to a second guidance element of the second slide, the second guidance element has a second insert arranged axially displaceably in said second guidance element, and the insert of the second slide is connected to the optics carrier.

DETAILED DESCRIPTION OF THE INVENTION

Preferably, the X displacement unit comprises a second oblique rotation axis for balancing the pivot support along with the surgical microscope about this oblique axis extending at an angle to the Z direction, said angle being larger than 0 degrees and smaller than 90 degrees.

Regarding achievement of the first object, the inventor has recognized that electrification of the slide drives is useful in a first partial step toward solving the problem and enhancing convenience, and has thus provided, instead of or in addition to the balancing screws, electric drives that can be controlled by the surgeon in remotely operable fashion. Such electrification of the Y and Z slides is moreover not novel, especially since the OHS 4 and OHS 5 accessories of Mitaka comprise electrically drivable slides of this kind. The replacement of manually operable balancing screws with electric motors may be obvious per se. Such replacement would, however, be associated with the following remote-control elements: A switch for actuating the one electric motor, e.g. for the Y displacement, specifically in a +Y direction and a −Y direction, for example a toggle switch having a forward and a reverse direction; a further switch for actuating the other electric motor, e.g. for the Z displacement, specifically in a +Z direction and a −Z direction, for example a second toggle switch having a forward and a reverse direction. This is also the implementation used in the aforementioned stands of the Mitaka company.

With this obvious or known replacement of the existing balancing screws with two electric motors and one toggle switch for each one, the following intellectual effort would be required of the surgeon: for each a-b or c-d balancing procedure, he or she would need to locate the correct toggle switch in order to actuate it and therefore the correct electric motor.

Whereas this procedure is relatively logical in the case of the conventional MC1 because of the positioning of the balancing screws on the respective slides, such logic would be absent in the electrified version, especially if the switches were installed on the handle. That would be, however, the only advantageous place to locate them. Thus, either the surgeon would need to learn, laboriously, which toggle switch belongs to which displacement procedure, or the toggle switches would need to be correspondingly labeled. Labeling would, however, force the surgeon to read the label; in other words, he or she would deliberately need to turn his or her attention away from the surgical field and the surgical microscope. This is perceived as unpleasant and disadvantageous. For this reason, mere (obvious and known) electrification of the existing balancing screws is only suboptimal.

Recognizing this state of affairs, the inventor has made a second, nonobvious partial step. He has resolved operation of the two electric motors into a fundamental forward/reverse movement (i.e. now only one toggle switch having a + and a − direction) and an instruction for discrimination between the two electric motors. Operation thereby becomes simpler since the intellectual effort required is reduced. With one switch, a selection is made between the vertical or the horizontal balancing direction. This can be, for example, a switch of a different shape, i.e. it need not be toggle-shaped. It can have, for example, a geometrical shape such as to make clear to the operator that one switch position relates to a horizontal position and the other to a vertical position, so that it is "perceptible" that in the one switch position it is the Y displacement motor, and in the other switch position the Z displacement motor, that is energized. This could also be an acoustic switch that discriminates by way of the spoken word. With the other (toggle) switch, conversely, the respectively selected motor is driven forward or in reverse.

This nonobvious resolution of the manner in which control is applied to the electric motors requires less intellectual effort from the surgeon, and thus enhances operating convenience and speed.

The first object is thus achieved by way of this configuration according to the present invention.

A further development of the invention is created if the selector switch is also omitted, and if the surgeon is relieved of the task of operating the selector switch. The inventor arrives at this by providing in accordance with the invention, rather than a separate switch for changing over between the two balance positions, instead a sensor that automatically detects the particular balance position and accordingly connects the corresponding electric motors to the forward/reverse switch. The surgeon therefore now, according to the present invention, needs to operate only one switch. Based on the balance position arbitrarily selected by the surgeon, control is therefore automatically applied by means of a toggle switch to the correct electric motor.

A simple electrical implementation of this further development of the invention would be a solution using a position switch or limit switch. Relatively complex wiring would, however, be necessary for this. In addition, mechanical switches are subject to mechanical wear, with the result that here as well, the inventor looked for a further improvement.

A very wide variety of electronic sensors are therefore possible as sensors usable according to the present invention. According to a further development of the invention, however, the inventor has discovered a particular sensor that is notable for its simple manner of operation, robust construction, and good availability: according to the present invention, a static acceleration sensor is used. The following type is preferably utilized: ADXL322 manufactured by Analog Devices, Inc.

This sensor indicates the selected position with high resolution and in wear-free fashion, and can thus discriminate effectively between the two balance positions with no need for the surgeon to input information regarding the balance position selected.

Wiring can thus be minimized with the use of a static acceleration sensor of this kind. Along with the changeover electronics for the two electric motors, it can be integrated directly into one of the slides and thus directly into the electric motors.

Further details of this invention may be inferred from the Claims and from the Figures and their description.

The inventor has further recognized that in order to achieve the second stated object, weight must be reduced at least in the region of the optics carrier, without limiting movements for a precise balancing procedure. In particular, the intention was to remove the additional compensation weight. If this were successful, then in combination with the aforesaid manner of achieving the first object, an ideal design for the surgical microscope would be found. This second object is not achieved or suggested by any of the known balancing apparatuses, especially because this object had not hitherto been stated in any of the known documents (including DE 10133018 A1) of the existing art. In addition to replacement of the add-on weight, a further intention is therefore to prioritize weight saving, cost reduction, and smooth operation of the stand.

This second object is achieved, according to the present invention, by a balancing apparatus wherein the first and second slides are integrated into a cross-slide that is rotatable around a rotation axis relative to the pivot support,
wherein the first slide is arranged as part of the Y displacement unit transversely to the rotation axis alongside the pivot support and the second slide is arranged between the first slide and the optics carrier as part of the Z displacement unit so that the weight of the second slide acts as a compensation weight across the rotation axis.

The invention will be further explained, symbolically and by way of example, with reference to the attached drawings. It is understood that the actions for achieving the first object are integrated into FIGS. 1 to 3 below, although not explicitly visible.

DETAILED DESCRIPTION OF THE DRAWINGS

Figure 1:
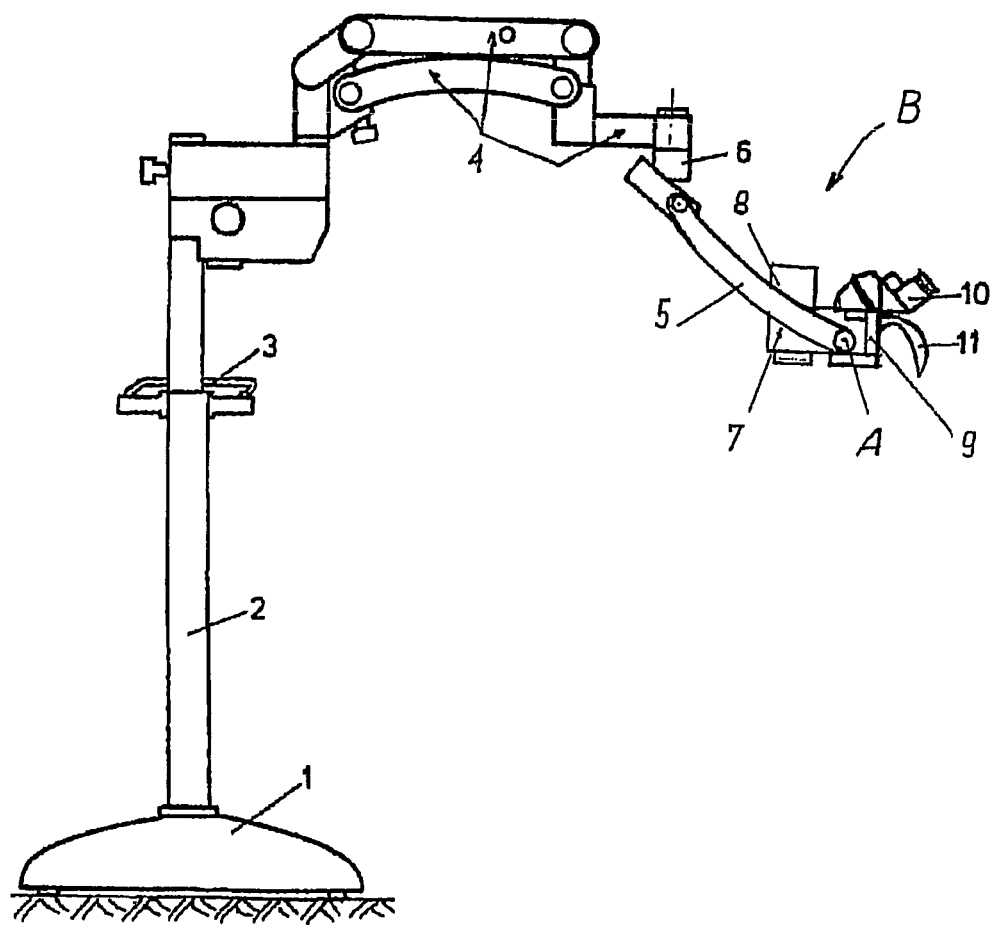
FIG. 1 is a side view of an overall configuration of a stand for and having the surgical microscope having a balancing apparatus according to the present invention.

FIG. 1 is a side view depicting a schematic overall structure of an exemplifying embodiment of the stand having a surgical microscope. It is equipped with a stand base 1 (known per se), a vertical support 2, and a grip 3 for moving the stand. A horizontal support unit 4 known from the MC1 is arranged at the upper end of vertical support 2. In this embodiment, an X displacement unit 6 is arranged at the free end of horizontal support unit 4, enabling displacement in the X direction of a pivot support 5 and with it Y and Z displacement units 7 and 8 installed at its lower end, as well as an optics carrier 9 mounted on Z displacement unit 8. The stand can be embodied as a floor or wall stand, or a ceiling mount. It is depicted as a floor stand merely by way of example. The X displacement unit 6 that is depicted derives from DE 10133018 A1 of the existing art. More details regarding it are provided therein, and reference is expressly made to this Application (incorporation by reference).

X, Y, and Z displacement units 6 to 8 together constitute a balancing apparatus B that is associated with pivot support 5. Manual balancing displacements, for example, can be carried out quickly and exactly by means of the specific configuration and arrangement of balancing apparatus B according to the present invention (see also FIG. 2). The eyepieces of the surgical microscope are labeled 10, and a handle for manual displacement of the surgical microscope is labeled 11.

Located on this handle 11 (in a manner not depicted in further detail) are, for example, a toggle switch for the forward-reverse switching instructions and a switch for discriminating between the balance positions. Alternatively or in accordance with a particular embodiment, only a forward-reverse switch (e.g. a toggle switch) is located on this handle 11, whereas discrimination between the balance positions is accomplished by way of an electronic sensor having corresponding electronics in the interior of optics carrier 9 or in the interior of balancing apparatus 7 or 8. The use of handle 11 as depicted is merely an example. It would also be possible advantageously, and in a manner known per se on the MC1 already mentioned, for a two-sided handle to be provided, i.e. one handle for the left hand and one for the right. It is usual also to provide on such handles (in a manner similar to motorcycle grips) electrical switch knobs or the like that enable, for example, selective release of brakes and/or application of control to the illumination system or the like. In the case of the present invention (first object), the forward-reverse switch and/or the selector switch can be located on one or both of these handles.

Figure 2:
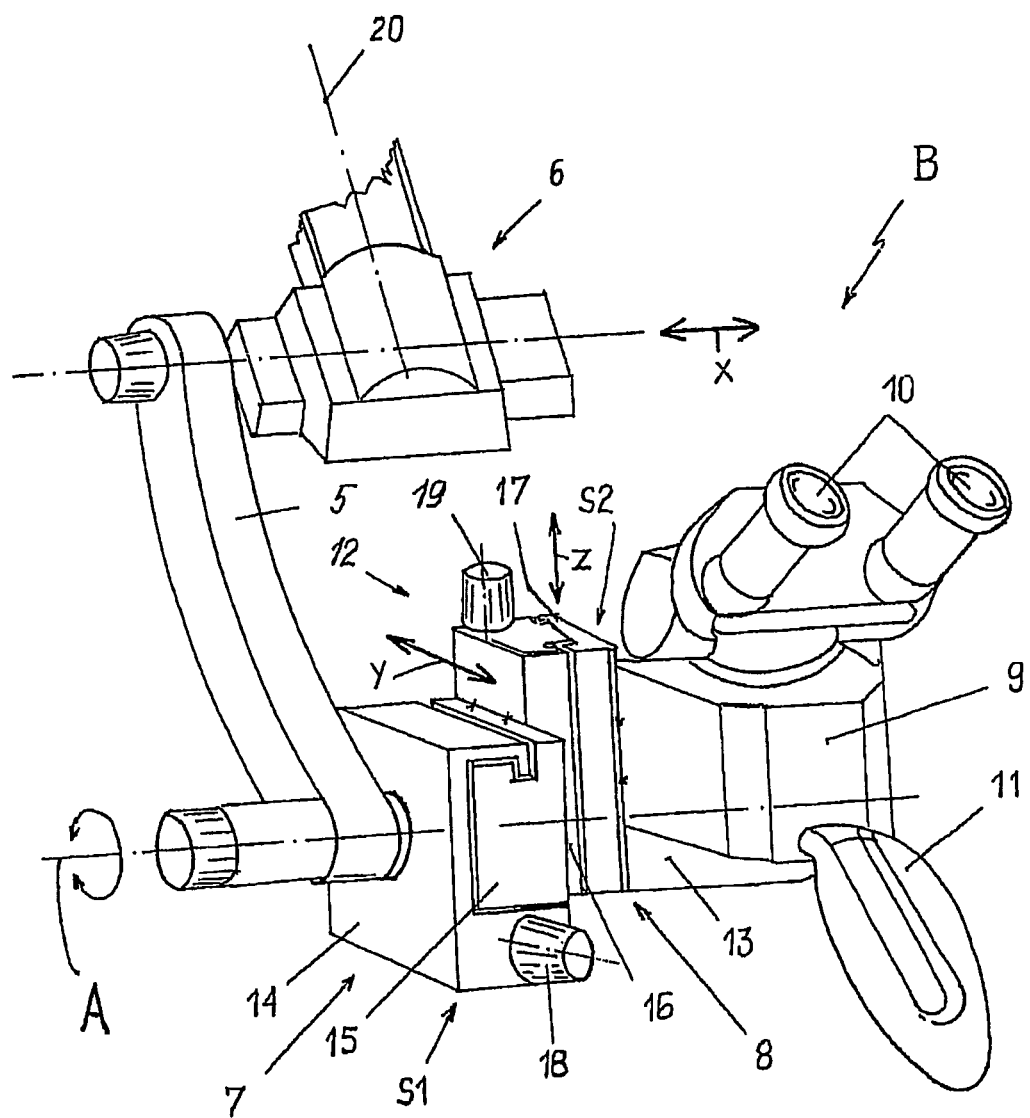
FIG. 2 is a perspective view, at enlarged scale, of a portion of the stand having the surgical microscope according to FIG. 1, and of the balancing apparatus.

FIG. 2 shows, in perspective, a portion of the structure of pivot support 5 and of the stand parts for the surgical microscope in the region of optics carrier 9, as well as balancing apparatus B itself. It is clearly apparent here that one portion of balancing apparatus B, i.e. X displacement unit 6 for horizontal displacement in the X direction, is arranged separately at the upper end of pivot support 5 (as in the embodiment according to FIG. 2 of DE 10133018 A1 cited above).

Leaving aside the novel discrimination and forward-reverse switching system, the essence of the manner in which the second object is achieved lies in the particular configuration and arrangement of the further parts of balancing apparatus B, i.e. Y displacement unit 7 for displacement in the Y direction, and Z displacement unit 8 for displacement in the Z direction, which are interconnected at the lower end of pivot support 5 and arranged rotatably about a horizontal rotation axis A and in a manner allowing immobilization in any rotational position that is established. For achievement of the first object it does not matter according to the present invention how the Y and Z displacement units are arranged. They could certainly also be arranged as they are on the MC1. According to the present invention (with regard to the manner of achieving the second object), Y displacement unit 7, and Z displacement unit 8 coacting therewith, of balancing apparatus B are preferably embodied as a cross-slide 12. A first slide S1 (horizontal arrow in FIG. 2) of cross-slide 12 is provided as part of Y displacement unit 7, and a second slide S2 (vertical arrow in FIG. 2) of cross-slide 12 is provided as part of Z displacement unit 8.

One important feature of the invention is the fact that first slide S1 of cross-slide 12 is arranged, as part of Y displacement unit 7, along rotation axis A directly alongside pivot support 5; and that second slide S2 of cross-slide 12 is located, as part of Z displacement unit 8, to the right of Y displacement unit 7 (see FIG. 2), where it carries a microscope holder 13. This arrangement is not, however, mandatory for achieving the invention solely in accordance with the first object, since even with a conventional (i.e. reversed; see MC1) arrangement, the new discrimination apparatus having a manually actuable switch, or electronically actuable switch on the slide construction in accordance with the MC1, an advantage for the surgeon is attainable in terms of operating convenience and easier balancing. An optics carrier 9 is held in microscope holder 13 and thus on second slide S2 of Z displacement unit 8. This configuration is merely preferable, since optics carrier 9 could also be connected directly to slide S2. What is visible in FIG. 2 of the surgical microscope itself is optics carrier 9, eyepieces 10, and handle 11.

Figure 3:
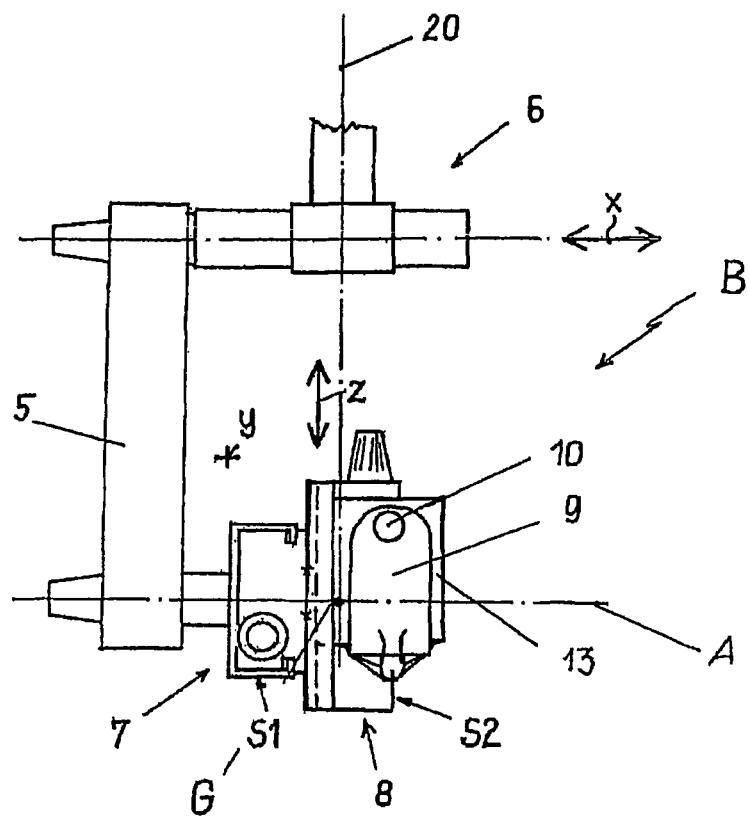
FIG. 3 is a schematic front view of the approach according to FIG. 2 viewed in the Y direction, with an eyepiece 10 depicted merely symbolically.

The exemplifying details of cross-slide 12 are visible in FIGS. 2 and 3. First slide S1 has a horizontal guidance element 14 and an insert 15 arranged therein in axially shiftable or displaceable fashion. Second slide S2 is equipped in similar fashion with a vertical guidance element 16 and an insert 17 displaceable axially therein. For coaction of the two slides S1 and S2 of cross-slide 12, horizontal insert 15 of slide S1 is connected to vertical guidance element 16 of slide S2 (FIG. 2). In this instance, microscope holder 13 is detachably or rigidly mounted on the vertically shiftable insert 17 of slide S2. Detachable mounting can provide a further balancing capability by the fact that microscope holder 13 or optics carrier 9 is embodied positionably relative to slide S2.

In FIG. 2, Y displacement unit 7, and Z displacement unit 8 coacting therewith, of balancing apparatus B are equipped with a respective knob 18, 19 for manual displacement and immobilization. In FIGS. 2 and 3, an oblique/vertical axis of the mechanism is labeled 20. Surgical microscope 9 with its pivot support 5 can be rotated about this axis 20 if the brake (not depicted) associated therewith is released. X displacement unit 6 serves for balancing the construction about this axis 20.

A "pivot support" is understood for purposes of the invention as that component or component group which is installed indirectly or directly on horizontal support unit 4 of the stand (FIG. 1) and which receives, via the (in principle, horizontal) rotation axis A, a microscope holder 13 in which optics carrier 9 is held.

FIG. 3 schematically depicts the arrangement according to the present invention of FIG. 2 in a front view. A completely balanced-out position of the surgical microscope in a vertical (normal) working position is symbolically shown here.

In this position, the common center of gravity G of optics carrier 9 (with the respective accessories) and of Y and Z displacement units 7 and 8 is located in axis A. This completely balanced-out configuration of the system is one principal goal to be achieved by the use of balancing apparatus B according to the present invention (second object) having the novel slide arrangement. Among many other aspects of the invention, particularly unique is the inventive arrangement of slide S1 (Y displacement) on axis A alongside pivot support 5, and the arrangement of slide S2 (Z displacement) on microscope holder 13. The effect that results is as follows: The weight of slide S2 now acts, in novel fashion, as a weight that is also balanced across axis A in the Y direction. It thus acts as a compensation weight, as can best be gathered from FIG. 1. As a result of this surprisingly simple action (exchanging the slides for the Y and the Z direction in terms of the known MC1 configuration), the use of an add-on weight becomes inapplicable. The weight of the Z slide is in fact in the range of approximately 3.5 kg, so that the slide of itself replaces the add-on weight practically exactly.

This invention is particularly ingenious because the Z slide corresponds approximately to the weight of the Y slide, since not only has a replacement been found for the compensation weight, but furthermore the entire weight of the surgical microscope, together with cross-slides S1 and S2, is kept the same even though a much improved balancing behavior (lower weight) is now achieved with the same Y-Z displaceability. The effect of surprise is intensified by the fact that for more than 10 years, the add-on weight in the MC1 was regarded by the technical community as the only possibility for practical balancing.

When the surgical microscope is in service, the invention thus guarantees the three displacements necessary for balancing the system so that optics carrier 9, together with the add-on units, can be positioned and balanced at any time, and the necessary movements can be performed in three principal directions. The three principal directions X, Y, and Z are to be understood (according to FIG. 3) as follows: the X direction as approximately left-right with respect to the observer, the Y direction as a front-back direction, and the Z direction as a direction of movement oriented up and down. Any conceivable movement or rotary positioning in three dimensions can of course be performed, for example manually using handle 11, by way of the linear displacements combined with a 360-degree rotation capability of optics carrier 9 about axis A and about axis 20.

The respective position of optics carrier 9 is to be established with reference to a patient or to the surgical field. In ENT procedures in particular, changes in position are often necessary in this context (at least more often than in brain operations). The balance behavior must be optimal regardless of the particular pivot position of the surgical microscope in three dimensions. The invention ensures this. At the same time, however, achievement of the first object facilitates not only balance behavior but also, explicitly the balancing procedure.

Thanks to balancing apparatus B according to the present invention, in particular cross-slide 12 that is proposed, slides S1 and S2 can be made smaller and lighter overall. During the balancing procedure, the weight displacement function results from the installation of slide S2, which is responsible for the vertical Z displacement of optics carrier 9, directly on microscope holder 13. The weight that needs to be carried by slide S2 is now made up only of the weight of the surgical microscope or optics carrier 9, and of microscope holder 13. An insert 15 of slide S1 responsible for the horizontal Y displacement is fixedly connected to guidance element 16 of slide S2 and also acts in weight-shifting fashion, since microscope holder 13, which receives optics carrier 9 (detachably, if necessary), is mounted on insert 17 (displaceable in the Z direction) of slide S2.

In the context of balancing apparatus B according to the present invention, the proposed construction and arrangement of cross-slide 12 has the advantage that the surgical microscope can be so precisely adjusted or balanced out that after complete balancing, center of gravity G of the surgical microscope, regardless of its configuration and add-on units and regardless of its particular pivot position, is always located in rotation axis A and in rotation axis 20. With this system the pivoting movement can therefore routinely be carried out more simply (without manipulation of add-on weights) and more easily (because of the lower total weight and hence lower frictional forces and resistance moments), and with higher working quality, than in the case of the existing art cited.

Based on experience so far, the present invention offers an improved surgical microscope that, in its balanced-out state, can be moved and balanced smoothly and, if necessary, with one hand. At the same time, however, it can also be adjusted exactly, quickly, and reliably by way of the electrical balance adjustment system as soon as add-on units are installed on or removed from the surgical microscope. The preparation phase for utilization of the surgical microscope can thus be significantly shortened. Refitting and rebalancing can now be performed quickly even during a procedure, if necessary. A drape now no longer impedes the adjusting procedure, and even during balancing the surgeon can concentrate on the surgical microscope and the surgical field.

A multiple-slide embodiment of the invention is also conceivable, along the lines of FIG. 3 of DE 10133018 A1 cited above, in which case X displacement unit 6 would also be arranged at the lower end of pivot support 5 in combination with Y and Z displacement units 7, 8 of balancing apparatus B. Here as well, however, a decisive factor for the invention in contradistinction to what is known would be the fact that at least the Z displacement unit (S2) and/or the X displacement unit functions as a compensation weight on microscope holder 13 about axis A. The more-compact design according to the present invention is thereby achievable without an add-on weight. If applicable, the vertically displaceable insert 17 of second Z slide S2, and optics carrier 9, can also be embodied integrally. The horizontally displaceable insert 15 of first Y slide S1 could also be manufactured from a single piece along with vertical guidance element 16 of second Z slide S2. The design would be further integrated by these actions.

In the symbolic depictions of the invention, rotary knobs 18 and 19 are indicated for the operation of slides S1 and S2, respectively. Instead of these, in terms of achievement of the first object electrical drives could also be provided. Such electrical drives can, however, also be provided in addition to rotary knobs 18, 19 (balancing screws) that are provided.

Figure 4:
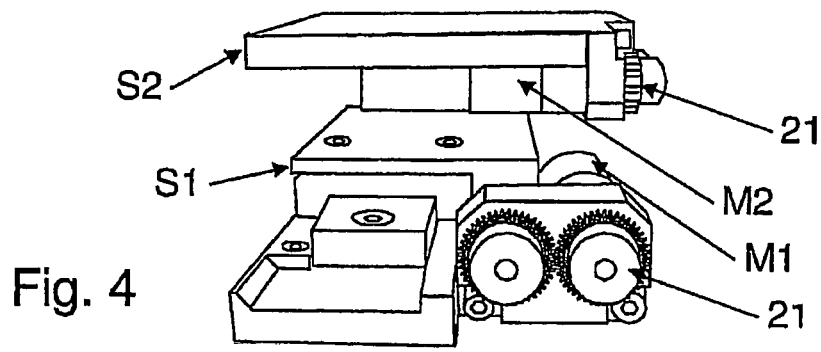
FIG. 4 is a side view of a cross-slide of the balancing apparatus having the two electric motors.

FIGS. 4 to 8 concern themselves more with the configuration achieving the first object. FIG. 4 is a side view showing the cross-slides (S1 and S2) with two electric motors M1 and M2. Because of the integrated design, motors M1 and M2 are placed into the interior of the respective slide S1 and S2. Motor force is applied elegantly, by means of a reversing gearbox 21, to the displacement spindles of slides S1 and S2. Also installed on slide S2 (although not visible) is a circuit board 22 having the requisite electronics for motors M1 and M2 and for sensor BS.

Figure 5:
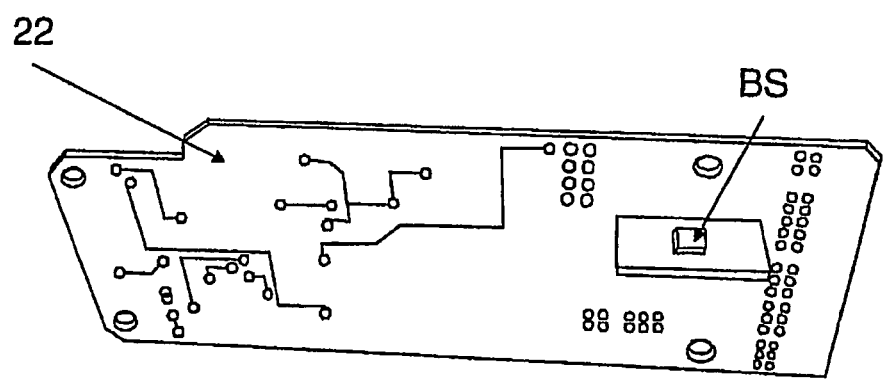
FIG. 5 shows a circuit board having a built-in sensor BS.

FIG. 5 shows the circuit board with sensor BS built into or onto it. Sensor BS sits on a bent holding plate of the circuit board. This holding plate is integrated into the holding plate or insert 17 of slide S2, as may be seen from FIG. 6. The latter shows a portion of slide S2 with circuit board 22 attached, so that sensor BS is integrated, and is thus effectively associated in geometrical terms, with slide S2. In addition, with this embodiment the sensor is well protected from mechanical loads.

Figure 6:
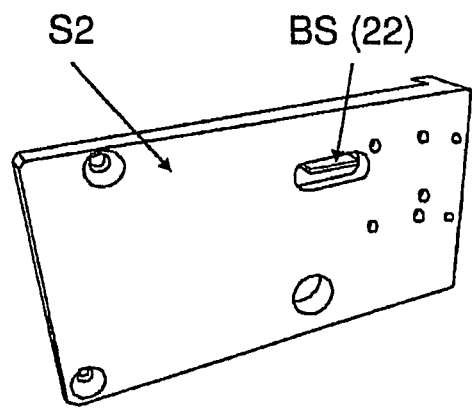
FIG. 6 shows a portion of slide S2 of the balancing apparatus with circuit board 22 built onto it, so that sensor BS is integrated.
Figure 7:
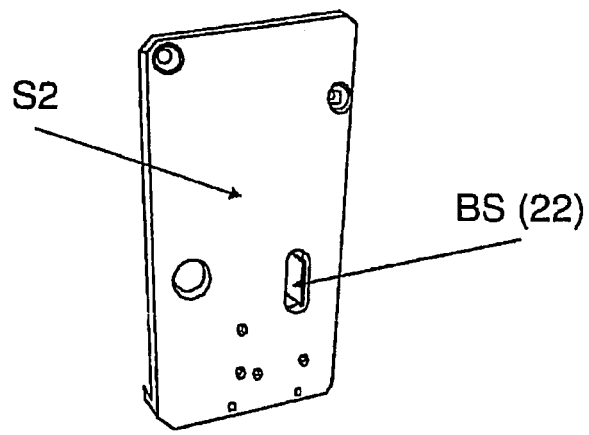
FIG. 7 shows the portion according to FIG. 6 in the vertical pivoted balance position.

FIG. 7 shows the same portion as FIG. 6, but in a pivoted vertical position. This elucidates the fact that the static acceleration sensor can readily discriminate between the two positions (horizontal and vertical), and can accordingly apply control to the respectively responsible motor M1 or M2. The operator (surgeon) now needs only to indicate the direction and duration of the displacement movement (balancing movement); the single forward-reverse switch VRS is sufficient for this.

Figure 8:
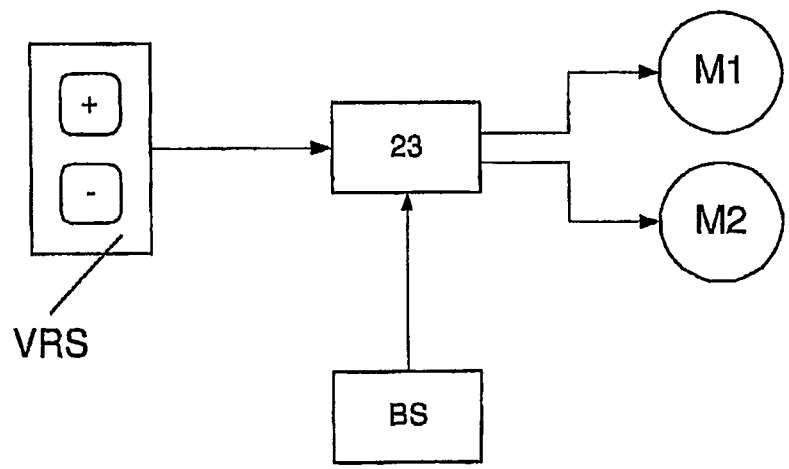
FIG. 8 shows the wiring layout according to the present invention, with a forward-reverse switch VRS and an electronic changeover switch 23.

FIG. 8 shows the circuit layout according to the present invention, with forward-reverse switch VRS and an electronic changeover switch 23 for discriminated application of control to motors M1 and M2.

The invention is, of course, not limited to the exemplifying embodiments that are depicted and described. Further embodiments and combinations are also conceivable on the basis of the disclosure, within the scope of protection that is claimed. For example, a manually actuable rotary balancing knob could be installed on one of the gears of the reversing gearbox so that balancing is possible even in the case of a power failure.

The Parts List below, like the formulation of the Claims, is a constituent of the disclosure.

Lastly, be it noted also that in the jargon used by those skilled in the art and by surgeons, the Y-Z slide is often referred to as an A-B slide. The X slide is then frequently referred to as a C slide.

Reference is furthermore made to U.S. patent application Ser. No. 12/371,440 filed Feb. 13, 2009 and U.S. application Ser. No. 12/371,492 filed Feb. 13, 2009, the disclosure of which is deemed to be disclosed herein especially for combinations of the technical teachings.

List of Component Parts
1 Stand base
2 Vertical support
3 Grip
4 Horizontal support unit
5 Pivot support
6 X displacement unit
7 Y displacement unit
8 Z displacement unit
9 Optics carrier
10 Eyepiece
11 Handle
12 Cross-slide
13 Microscope holder
14 Guidance element
15 Insert
16 Guidance element
17 Insert
18 Knob
19 Knob
20 Vertical oblique axis
21 Reversing gearbox
22 Circuit board of electronics for motors M1, M2
23 Electronic changeover switch for the two motors M1, M2
A Rotation axis (A axis)
B Balancing apparatus
BS Discrimination sensor
DS Selector switch
G Common center of gravity
M1 Motor
M2 Motor
VRS Forward-reverse switch
X X direction
Y Y direction
Z Z direction

The invention claimed is:

1. A balancing apparatus for a surgical microscope for balancing an optics carrier that carries optics of the surgical microscope, said optics carrier being held via a pivot support at a stand such that the balancing compensates for the use with and without a microscope holder holding the surgical microscope and with and without add-on units, wherein the balancing apparatus is arranged at the free end of the pivot support and comprises:

a Y displacement unit comprising a first slide for displacement of the optics carrier in a Y direction, the first slide being driven by a remotely controllable first motor;

a Z displacement unit comprising a second slide for displacement of the optics carrier in a Z direction by a second motor;

a selector switch enabling an operator to select powering either the first motor or the second motor; and a forward-reverse switch enabling an operator to select either the forward or the reverse driving mode for the motor powered by the selector switch and consequently enabling the operator to select either the forward or the reverse driving mode of the first or second slide, respectively; wherein the first and second slides are integrated into a cross-slide that is rotatable around a rotation axis relative to the pivot support, wherein the first slide is arranged as part of the Y displacement unit transversely to the rotation axis alongside the pivot support and the second slide is arranged between the first slide and the optics carrier as part of the Z displacement unit, so that the weight of the second slide acts as a compensation weight across the rotation axis for locating a common center of gravity G of the optics carrier with respective accessories and the Y and Z displacement units in the rotation axis; and the first slide of the cross-slide has a first guidance element and a first insert axially displaceable in that first guidance element, the first insert is secured to a second guidance element of the second slide, the second guidance element has a second insert arranged axially displaceably in said second guidance element, and the insert of the second slide is connected to the optics carrier.

2. The balancing apparatus according to claim 1, wherein the selector switch comprises at least one sensor for determining the balance position of the surgical microscope and as a result of the determined balance position for selecting to power either the first motor or the second motor.

3. The balancing apparatus according to claim 2, wherein the at least one sensor comprises a limit switch for determining the balance position in the Y and the Z direction.

4. The balancing apparatus according to claim 2, wherein the at least one sensor is at least one of an electronic position sensor, an angle sensor and a static acceleration sensor.

5. The balancing apparatus according to claim 2, wherein the optics carrier along with the axially displaceable slide of the Z displacement unit is held by a microscope holder that carries in integrated fashion at least one of electronics and sensor for the motors.

6. The balancing apparatus according to claim 1, wherein a sensor, with its electronics, is integrated into one of the optics carrier and one of the slides.

7. The balancing apparatus according to claim 1, wherein the optics carrier is connected displaceably to the second slide.

8. The balancing apparatus according to claim 1, wherein the second insert of the second slide of the cross-slide and the optics carrier are integrally formed.

9. The balancing apparatus according to claim 1, wherein the first insert of the first slide is integrally formed with the second guidance element of the second slide.

10. The balancing apparatus according to claim 1, comprising an X displacement unit for balancing the pivot support along with the surgical microscope.

11. The balancing apparatus according to claim 10, wherein the X displacement unit comprises a second oblique rotation axis for balancing the pivot support along with the surgical microscope about this oblique axis extending at an angle to the Z direction, said angle being larger than 0 degrees and smaller than 90 degrees.

12. The balancing apparatus of claim 1, further comprising a static acceleration sensor to detect a pivotal position of a surgical microscope about a rotation axis in a balancing process for balancing the surgical microscope.

* * * * *